United States Patent
Baldwin et al.

(10) Patent No.: US 10,045,732 B2
(45) Date of Patent: Aug. 14, 2018

(54) MEASURING MUSCLE EXERTION USING BONE CONDUCTION

(71) Applicant: AT&T Intellectual Property I, L.P., Atlanta, GA (US)

(72) Inventors: Christopher Baldwin, Algonquin, IL (US); Brian S. Amento, Morris Plains, NJ (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 146 days.

(21) Appl. No.: 14/482,101

(22) Filed: Sep. 10, 2014

(65) Prior Publication Data
US 2016/0066834 A1    Mar. 10, 2016

(51) Int. Cl.
*A61B 5/00*    (2006.01)

(52) U.S. Cl.
CPC .......... *A61B 5/4519* (2013.01); *A61B 5/0051* (2013.01); *A61B 5/0022* (2013.01); *A61B 5/4504* (2013.01); *A61B 5/486* (2013.01); *A61B 5/7246* (2013.01)

(58) Field of Classification Search
CPC ..... A61B 5/4519; A61B 5/0051; A61B 5/486; A61B 5/7246; A61B 5/0022; A61B 2560/0475
See application file for complete search history.

(56) References Cited

U.S. PATENT DOCUMENTS

| | | | |
|---|---|---|---|
| 3,629,521 A | 12/1971 | Puharich et al. | |
| 4,048,986 A * | 9/1977 | Ott | A61B 5/117 340/5.82 |
| 4,340,778 A | 7/1982 | Cowans et al. | |

(Continued)

FOREIGN PATENT DOCUMENTS

| | | |
|---|---|---|
| AU | 2003257031 | 2/2004 |
| AU | 2007200415 | 8/2007 |

(Continued)

OTHER PUBLICATIONS

Harrison et al., "Acoustic Barcodes: Passive, Durable and Inexpensive Notched Identification Tags," Proceedings of the 25th Annual ACM Symposium on User Interface Software and Technology, Oct. 7-10, 2012, ACM, Cambridge, MA.

(Continued)

*Primary Examiner* — Sean Dougherty
(74) *Attorney, Agent, or Firm* — Hartman & Citrin LLC

(57) ABSTRACT

Concepts and technologies are disclosed herein for measuring user exertion via bone conduction. According to one aspect, a device can generate a measurement signal. The device can cause a transducer to transmit the measurement signal through a body of a user. The device can receive, via the transducer, a modified measurement signal. The modified measurement signal can include the measurement signal as modified by the body of the user. The device can compare the modified measurement signal to a modified baseline signal. The device can determine, based on a result of comparing the modified measurement signal to the modified baseline signal, a level of exertion experienced by the user while the measurement signal was transmitted through the body of the user.

14 Claims, 6 Drawing Sheets

(56) References Cited

U.S. PATENT DOCUMENTS

| | | | |
|---|---|---|---|
| 4,421,119 A | 12/1983 | Pratt | |
| 4,720,607 A | 1/1988 | de Moncuit | |
| 4,754,763 A * | 7/1988 | Doemland | A61B 5/4504 600/552 |
| 4,799,498 A | 1/1989 | Collier | |
| 4,988,981 A | 1/1991 | Zimmerman et al. | |
| 5,024,239 A * | 6/1991 | Rosenstein | A61B 5/0051 600/552 |
| 5,073,950 A | 12/1991 | Colbert et al. | |
| 5,125,313 A | 6/1992 | Hiyoshi et al. | |
| 5,319,747 A | 6/1994 | Gerrissen et al. | |
| 5,327,506 A | 7/1994 | Stites, III | |
| 5,368,044 A | 11/1994 | Cain et al. | |
| 5,495,241 A | 2/1996 | Doing et al. | |
| 5,615,681 A | 4/1997 | Ohtomo | |
| 5,664,227 A | 9/1997 | Mauldin et al. | |
| 5,720,290 A * | 2/1998 | Buhler | A61B 5/4504 600/449 |
| 5,749,363 A * | 5/1998 | Ishii | A61B 8/0875 600/453 |
| 5,766,208 A | 6/1998 | Mcewan | |
| 5,810,731 A | 9/1998 | Sarvazyan et al. | |
| 5,813,406 A | 9/1998 | Kramer et al. | |
| 5,836,876 A | 11/1998 | Dimarogonas | |
| 6,024,711 A * | 2/2000 | Lentle | A61B 8/0875 600/586 |
| 6,115,482 A | 9/2000 | Sears et al. | |
| 6,135,951 A | 10/2000 | Richardson et al. | |
| 6,151,208 A | 11/2000 | Bartlett | |
| 6,154,199 A | 11/2000 | Butler | |
| 6,213,934 B1 * | 4/2001 | Bianco | A61B 5/053 600/14 |
| 6,234,975 B1 | 5/2001 | Mcleod et al. | |
| 6,336,045 B1 * | 1/2002 | Brooks | A61B 5/053 600/407 |
| 6,380,923 B1 | 4/2002 | Fukumoto | |
| 6,396,930 B1 | 5/2002 | Vaudrey et al. | |
| 6,409,684 B1 | 6/2002 | Wilk | |
| 6,507,662 B1 | 1/2003 | Brooks | |
| 6,515,669 B1 | 2/2003 | Mohri | |
| 6,580,356 B1 | 6/2003 | Alt et al. | |
| 6,589,287 B2 | 7/2003 | Lundborg | |
| 6,631,197 B1 | 10/2003 | Taenzer | |
| 6,754,472 B1 | 6/2004 | Williams et al. | |
| 6,783,501 B2 | 8/2004 | Takahashi et al. | |
| 6,844,660 B2 | 1/2005 | Scott | |
| 6,898,299 B1 | 5/2005 | Brooks | |
| 6,912,287 B1 | 6/2005 | Fukumoto et al. | |
| 7,010,139 B1 | 3/2006 | Smeehuyzen | |
| 7,123,752 B2 | 10/2006 | Kato et al. | |
| 7,148,879 B2 | 12/2006 | Amento et al. | |
| 7,198,607 B2 | 4/2007 | Jamsen | |
| 7,206,423 B1 | 4/2007 | Feng et al. | |
| 7,232,416 B2 * | 6/2007 | Czernicki | A61B 7/006 482/6 |
| 7,370,208 B2 | 5/2008 | Levin et al. | |
| 7,405,725 B2 | 7/2008 | Mohri et al. | |
| 7,536,557 B2 | 5/2009 | Murakami et al. | |
| 7,539,533 B2 | 5/2009 | Tran | |
| 7,615,018 B2 | 11/2009 | Nelson et al. | |
| 7,625,315 B2 | 12/2009 | Hickman | |
| 7,648,471 B2 | 1/2010 | Hobson | |
| 7,671,351 B2 | 3/2010 | Setlak et al. | |
| 7,708,697 B2 | 5/2010 | Wilkinson et al. | |
| 7,760,918 B2 | 7/2010 | Bezvershenko et al. | |
| 7,778,848 B1 | 8/2010 | Reeves | |
| 7,796,771 B2 | 9/2010 | Calhoun et al. | |
| 7,878,075 B2 | 2/2011 | Johansson et al. | |
| 7,914,468 B2 | 3/2011 | Shalon et al. | |
| 7,918,798 B2 * | 4/2011 | Wu | A61B 8/0875 600/437 |
| 8,023,669 B2 | 9/2011 | Segev et al. | |
| 8,023,676 B2 | 9/2011 | Abolfathi et al. | |
| 8,031,046 B2 | 10/2011 | Franza et al. | |
| 8,098,129 B2 | 1/2012 | Falck et al. | |
| 8,196,470 B2 | 6/2012 | Gross et al. | |
| 8,200,289 B2 | 6/2012 | Joo et al. | |
| 8,253,693 B2 | 8/2012 | Buil et al. | |
| 8,270,637 B2 | 9/2012 | Abolfathi | |
| 8,270,638 B2 | 9/2012 | Abolfathi et al. | |
| 8,312,660 B1 | 11/2012 | Fujisaki | |
| 8,348,936 B2 | 1/2013 | Trembly et al. | |
| 8,421,634 B2 | 4/2013 | Tan et al. | |
| 8,467,742 B2 | 6/2013 | Hachisuka et al. | |
| 8,482,488 B2 | 7/2013 | Jannard | |
| 8,491,446 B2 | 7/2013 | Hinds et al. | |
| 8,500,271 B2 | 8/2013 | Howell et al. | |
| 8,521,239 B2 | 8/2013 | Hosoi et al. | |
| 8,540,631 B2 | 9/2013 | Penner et al. | |
| 8,542,095 B2 | 9/2013 | Kamei | |
| 8,560,034 B1 | 10/2013 | Diab et al. | |
| 8,594,568 B2 | 11/2013 | Falck | |
| 8,750,852 B2 | 6/2014 | Forutanpour et al. | |
| 8,908,894 B2 * | 12/2014 | Amento | H04K 1/00 381/151 |
| 8,922,427 B2 | 12/2014 | Dehnie et al. | |
| 9,031,293 B2 | 5/2015 | Kalinli-Akbacak | |
| 9,386,962 B2 * | 7/2016 | Dahl | A61B 8/0875 |
| 2001/0013546 A1 | 8/2001 | Ross | |
| 2001/0051776 A1 | 12/2001 | Lenhardt | |
| 2003/0048915 A1 | 3/2003 | Bank | |
| 2003/0066882 A1 | 4/2003 | Ross | |
| 2003/0125017 A1 | 7/2003 | Greene et al. | |
| 2003/0133008 A1 | 7/2003 | Stephenson | |
| 2004/0152440 A1 | 8/2004 | Yoda et al. | |
| 2005/0207599 A1 | 9/2005 | Fukumoto et al. | |
| 2005/0210269 A1 | 9/2005 | Tiberg | |
| 2006/0018488 A1 | 1/2006 | Viala et al. | |
| 2006/0132455 A1 | 6/2006 | Rimas-Ribikauskas | |
| 2006/0149337 A1 | 7/2006 | John | |
| 2007/0012507 A1 | 1/2007 | Lyon | |
| 2007/0142874 A1 | 6/2007 | John | |
| 2008/0064955 A1 | 3/2008 | Miyajima | |
| 2008/0084859 A1 | 4/2008 | Sullivan | |
| 2008/0223925 A1 | 9/2008 | Saito et al. | |
| 2008/0260211 A1 | 10/2008 | Bennett et al. | |
| 2009/0149722 A1 | 6/2009 | Abolfathi et al. | |
| 2009/0228791 A1 | 9/2009 | Kim | |
| 2009/0234262 A1 | 9/2009 | Reid, Jr. et al. | |
| 2009/0287485 A1 | 11/2009 | Glebe | |
| 2009/0289958 A1 | 11/2009 | Kim et al. | |
| 2009/0304210 A1 | 12/2009 | Weisman | |
| 2009/0309751 A1 | 12/2009 | Kano et al. | |
| 2010/0016741 A1 | 1/2010 | Mix et al. | |
| 2010/0066664 A1 | 3/2010 | Son et al. | |
| 2010/0137107 A1 | 6/2010 | Jamsa et al. | |
| 2010/0162177 A1 | 6/2010 | Eves et al. | |
| 2010/0168572 A1 | 7/2010 | Sliwa et al. | |
| 2010/0286571 A1 | 11/2010 | Allum et al. | |
| 2010/0297944 A1 | 11/2010 | Lee | |
| 2010/0315206 A1 | 12/2010 | Schenk et al. | |
| 2010/0316235 A1 | 12/2010 | Park et al. | |
| 2010/0328033 A1 | 12/2010 | Kamei | |
| 2011/0022025 A1 | 1/2011 | Savoie et al. | |
| 2011/0125063 A1 | 5/2011 | Shalon et al. | |
| 2011/0134030 A1 | 6/2011 | Cho | |
| 2011/0135106 A1 | 6/2011 | Yehuday et al. | |
| 2011/0137649 A1 | 6/2011 | Rasmussen et al. | |
| 2011/0152637 A1 | 6/2011 | Kateraas et al. | |
| 2011/0155479 A1 | 6/2011 | Oda | |
| 2011/0227856 A1 | 9/2011 | Corroy et al. | |
| 2011/0245669 A1 | 10/2011 | Zhang | |
| 2011/0255702 A1 | 10/2011 | Jensen | |
| 2011/0260830 A1 | 10/2011 | Weising | |
| 2011/0269601 A1 | 11/2011 | Nelson et al. | |
| 2011/0276312 A1 * | 11/2011 | Shalon | A61B 5/11 702/187 |
| 2011/0280239 A1 | 11/2011 | Tung et al. | |
| 2011/0282662 A1 * | 11/2011 | Aonuma | G10L 17/26 704/231 |
| 2012/0010478 A1 | 1/2012 | Kinnunen et al. | |
| 2012/0011990 A1 | 1/2012 | Mann | |
| 2012/0058859 A1 | 3/2012 | Elsom-Cook et al. | |

(56) References Cited

U.S. PATENT DOCUMENTS

| | | | |
|---|---|---|---|
| 2012/0065477 | A1 | 3/2012 | Enomoto |
| 2012/0065506 | A1 | 3/2012 | Smith |
| 2012/0143693 | A1 | 6/2012 | Chung et al. |
| 2012/0202479 | A1 | 8/2012 | Sugitani et al. |
| 2012/0212441 | A1 | 8/2012 | Christiansson et al. |
| 2012/0280900 | A1 | 11/2012 | Wang et al. |
| 2012/0290832 | A1 | 11/2012 | Antequera Rodriguez et al. |
| 2013/0034238 | A1 | 2/2013 | Abolfathi |
| 2013/0041235 | A1 | 2/2013 | Rogers et al. |
| 2013/0097292 | A1 | 4/2013 | Yoakum et al. |
| 2013/0119133 | A1 | 5/2013 | Michael et al. |
| 2013/0120458 | A1 | 5/2013 | Celebisoy et al. |
| 2013/0135223 | A1 | 5/2013 | Shai |
| 2013/0142363 | A1 | 6/2013 | Amento et al. |
| 2013/0170471 | A1 | 7/2013 | Nix |
| 2013/0171599 | A1 | 7/2013 | Bleich et al. |
| 2013/0173926 | A1 | 7/2013 | Morese et al. |
| 2013/0212648 | A1 | 8/2013 | Tietjen et al. |
| 2013/0215060 | A1 | 8/2013 | Nakamura |
| 2013/0225915 | A1 | 8/2013 | Redfield et al. |
| 2013/0225940 | A1 | 8/2013 | Fujita et al. |
| 2013/0257804 | A1 | 10/2013 | Vu et al. |
| 2013/0278396 | A1 | 10/2013 | Kimmel |
| 2013/0288655 | A1 | 10/2013 | Foruntanpour et al. |
| 2013/0346620 | A1 | 12/2013 | Gizis et al. |
| 2014/0009262 | A1 | 1/2014 | Robertson et al. |
| 2014/0028604 | A1 | 1/2014 | Morinaga et al. |
| 2014/0097608 | A1 | 4/2014 | Buzhardt et al. |
| 2014/0099991 | A1 | 4/2014 | Cheng et al. |
| 2014/0107531 | A1 | 4/2014 | Baldwin |
| 2014/0156854 | A1 | 6/2014 | Gaetano, Jr. |
| 2014/0168093 | A1 | 6/2014 | Lawrence |
| 2014/0168135 | A1 | 6/2014 | Saukko et al. |
| 2014/0174174 | A1 | 6/2014 | Uehara et al. |
| 2014/0188561 | A1 | 7/2014 | Tenbrock et al. |
| 2014/0210791 | A1 | 7/2014 | Hanauer et al. |
| 2014/0240124 | A1 | 8/2014 | Bychkov |
| 2014/0035884 | A1 | 3/2015 | Oh et al. |
| 2015/0084011 | A1 | 3/2015 | Park et al. |
| 2015/0092962 | A1 | 4/2015 | Amento et al. |
| 2015/0120465 | A1 | 4/2015 | Baldwin et al. |
| 2015/0128094 | A1 | 5/2015 | Baldwin et al. |
| 2015/0137936 | A1 | 5/2015 | Baldwin et al. |
| 2015/0137960 | A1 | 5/2015 | Baldwin et al. |
| 2015/0138062 | A1 | 5/2015 | Baldwin et al. |
| 2015/0150116 | A1 | 5/2015 | Baldwin et al. |
| 2015/0199950 | A1 | 7/2015 | Heiman et al. |

FOREIGN PATENT DOCUMENTS

| | | |
|---|---|---|
| CA | 1207883 | 7/1986 |
| EP | 0712114 | 5/1996 |
| EP | 0921753 | 6/1999 |
| EP | 1436804 | 2/2004 |
| EP | 2312997 | 4/2011 |
| EP | 2643981 | 5/2012 |
| EP | 2483677 | 8/2012 |
| GB | 2226931 | 7/1990 |
| GB | 2348086 | 9/2000 |
| JP | 02249017 | 10/1990 |
| JP | 04-317638 A | 11/1992 |
| JP | 2003058190 | 2/2003 |
| JP | 2005142729 | 6/2005 |
| JP | 2010210730 | 9/2010 |
| KR | 20100056688 | 10/1990 |
| TW | 200946887 | 8/1997 |
| WO | WO 8201329 | 4/1982 |
| WO | WO 9601585 | 1/1996 |
| WO | WO 2003033882 | 4/2003 |
| WO | WO 2006094372 | 9/2006 |
| WO | WO 2009001881 | 12/2008 |
| WO | WO 2010045158 | 4/2010 |
| WO | WO 2012168534 | 12/2012 |

OTHER PUBLICATIONS

Yoo et al., "Analysis of Body Sensor Network Using Human Body as the Channel," Proceedings of the ICST $3^{rd}$ International Conference on Body Area Networks, 2008, Institute for Computer Sciences, Social-Informatics and Telecommunications Engineering.

Harrison et al., "Skinput: Appropriating the Body as an Input Surface," Proceedings of the SIGCHI Conference on Human Factors in Computing Systems, Apr. 10-15, 2010, ACM, Atlanta, GA.

Mujibiya et al., "The Sound of Touch: On-body Touch and Gesture Sensing Based on Transdermal Ultrasound Propagation," Proceedings of the 2013 ACM International Conference on Interactive Tabletops and Surfaces, Oct. 6-9, 2013, ACM, St. Andrews, United Kingdom.

Ni et al., "Disappearing Mobile Devices," Proceedings of the $22^{nd}$ Annual ACM Symposium on User Interface Software and Technology, Oct. 4-7, 2009, ACM, Victoria, British Columbia, Canada.

Zhong et al., "OsteoConduct: Wireless Body-Area Communication based on Bone Conduction," Proceeding of the ICST 2nd International Conference on Body Area Networks, BodyNets 2007.

Travis et al., "Hambone: A bio-acoustic gesture interface," 2007 11th IEEE International Symposium on Wearable Computers, 2007.

Scanlon, Michael V. Acoustic sensor for health status monitoring. Army Research Lab Aberdeen Proving Ground MD, 1998.

Yamada, Guillaume Lopez; Masaki Shuzo; Ichiro. "New healthcare society supported by wearable sensors and information mapping-based services." International Journal of Networking and Virtual Organisations 9.3 (2011): 233-247.

Scanlon, Michael V. "Acoustic sensors in the helmet detect voice and physiology." AeroSense 2003. International Society for Optics and Photonics, 2003.

Amento et al., "The Sound of One Hand: a Wrist-Mounted Bio-Acoustic Fingertip Gesture Interface," Short Talk: It's All About Sound, CHI 2002.

"Kinect Gestures," retrieved from http://support.xbox.com/en-US/xbox-360/kinect/body-controller on Oct. 24, 2013.

Mark Billinghurst, "Chapter 14: Gesture Based Interaction," Haptic Input, Aug. 24, 2011.

Kompis, Martin, and Rudolf Haeusler, "Electromagnetic interference of bone-anchored hearing aids by cellular phones revisited," Acta oto-laryngologica 122.5, 2002, 510-512.

T. Scott Saponas, et al., "Enabling always-available input with muscle-computer interfaces," Proceedings of the 22nd Annual ACM Symposium on User Interface Software and Technology, ACM, 2009.

Jao Henrique Donker, "The Body as a communication medium," 2009.

Sang-Yoon Chang, et al., "Body Area Network Security: Robust Key Establishment Using Human Body Channel," retrieved from https://www.usenix.org/system/files/conference/healthsec12/healthsec12-final15.pdf on Oct. 16, 2013.

Vidya Bharrgavi, et al., "Security Solution for Data Integrity in Wireless BioSensor Networks," Distributed Computing Systems Workshops, 2007, ICDCSW'07, 27th International Conference, IEEE, 2007.

Daniel Halperin, et al., "Pacemakers and Implantable Cardiac Defibrillators: Software Radio Attacks and Zero-Power Defenses," Security and Privacy, SP 2008, IEEE Symposium, IEEE, 2008.

Carmen C. Y. Poon, et al., "A Novel Biometrics Method to Secure Wireless Body Area Sensor Networks for Telemedicine and M-Health," Communications Magazine, IEEE 44.4, 2006, 73-81.

Zicheng Liu, et al., "Direct Filtering for Air-and Bone-Conductive Microphones," Multimedia Signal Processing, 2004 IEEE 6th Workshop, IEEE, 2004.

Hinckley, Ken, and Hyunyoung Song, "Sensor synaesthesia: touch in motion, and motion in touch." Proceedings of the SIGCHI Conference on Human Factors in Computing Systems. ACM, 2011.

Hinge, Dhanashree, and S. D. Sawarkar. "Mobile to Mobile data transfer through Human Area Network." IJRCCT 2.11 (2013): 1181-1184.

(56) References Cited

OTHER PUBLICATIONS

Park, Duck Gun, et al. "TAP: touch-and-play." Proceedings of the SIGCHI conference on Human Factors in computing systems. ACM, 2006.
Ruiz, J. Agud, and Shigeru Shimamoto. "A study on the transmission characteristics of the human body towards broadband intra-body communications." Consumer Electronics, 2005.(ISCE 2005). Proceedings of the Ninth International Symposium on. IEEE, 2005.
Nagai, Ryoji, et al. "Near-Field Coupling Communication Technology for Human-Area Networking." Proc. Conf. on Information and Communication Technologies and Applications (ICTA2011), International Institute of Informatics and Systems (IIIS). 2012.
Lipkova, Jolana, and Jaroslav Cechak. "Transmission of Information Using the Human Body."
Maruf, Md Hasan. "An Input Amplifier for Body-Channel Communication." (2013).
Rekimoto, Jun. "Gesturewrist and gesturepad: Unobtrusive wearable interaction devices." Wearable Computers, 2001. Proceedings. Fifth International Symposium on. IEEE, 2001.
U.S. Office Action dated Feb. 13, 2013 in U.S. Appl. No. 13/309,124.
U.S. Office Action dated Sep. 24, 2013 in U.S. Appl. No. 13/309,124.
U.S. Office Action dated Jan. 29, 2014 in U.S. Appl. No. 13/309,124.
U.S. Office Action dated Dec. 17, 2015 in U.S. Appl. No. 14/065,663.
U.S. Office Action dated Nov. 19, 2015 in U.S. Appl. No. 14/083,499.
U.S. Office Action dated Nov. 19, 2015 in U.S. Appl. No. 14/090,668.
U.S. Office Action dated Jan. 11, 2016 in U.S. Appl. No. 14/514,658.
U.S. Office Action dated Mar. 8, 2010 in U.S. Appl. No. 11/586,142.
U.S. Office Action dated Aug. 12, 2010 in U.S. Appl. No. 11/586,142.
Examiner's Answer to Appeal Brief dated Apr. 22, 2011 in U.S. Appl. No. 11/586,142.
Patent Board Decision on Appeal dated Sep. 25, 2014 in U.S. Appl. No. 11/586,142.
Notice of Allowance dated Dec. 18, 2014 in U.S. Appl. No. 11/586,142.
U.S. Office Action dated Feb. 25, 2016 in U.S. Appl. No. 14/072,126.
U.S. Notice of Allowance dated Apr. 4, 2016 in U.S. Appl. No. 14/083,499.
U.S. Notice of Allowance dated Mar. 21, 2016 in U.S. Appl. No. 14/090,668.
U.S. Office Action dated Mar. 16, 2016 in U.S. Appl. No. 14/482,087.
U.S. Office Action dated Mar. 10, 2016 in U.S. Appl. No. 14/482,091.
U.S. Office Action dated Aug. 25, 2015 in U.S. Appl. No. 11/586,142.
U.S. Office Action dated Aug. 25, 2015 in U.S. Appl. No. 14/083,094.
U.S. Office Action dated Jun. 25, 2015 in U.S. Appl. No. 14/083,110.
U.S. Appl. No. 14/482,087, filed Sep. 10, 2014.
U.S. Appl. No. 14/482,091, filed Sep. 10, 2014.
U.S. Appl. No. 14/482,078, filed Sep. 10, 2014.
U.S. Appl. No. 14/482,658, filed Oct. 15, 2014.
U.S. Office Action dated Jul. 7, 2016 in U.S. Appl. No. 14/072,126.
U.S. Notice of Allowance dated Jul. 12, 2016 in U.S. Appl. No. 14/482,091.
U.S. Office Action dated Aug. 17, 2016 in U.S. Appl. No. 15/161,499.
U.S. Notice of Allowance dated Oct. 7, 2016 in U.S. Appl. No. 15/224,808.
U.S. Office Action dated Oct. 20, 2017 in U.S. Appl. No. 14/482,078.
U.S. Office Action dated Dec. 14, 2016 in U.S. Appl. No. 14/561,549.
U.S. Office Action dated Apr. 7, 2017 in U.S. Appl. No. 14/065,663.
U.S. Office Action dated Jun. 1, 2017 in U.S. Appl. No. 14/482,078.
U.S. Office Action dated May 10, 2017 in U.S. Appl. No. 15/161,499.
U.S. Notice of Allowance dated Mar. 28, 2017 in U.S. Appl. No. 15/224,808.
U.S. Office Action dated Apr. 21, 2017 in U.S. Appl. No. 15/450,624.
U.S. Notice of Allowance dated Aug. 21, 2017 in U.S. Appl. No. 14/065,663.
U.S. Office Action dated Dec. 13, 2017 in U.S. Appl. No. 15/250,375.
U.S. Notice of Allowance dated Aug. 22, 2017 in U.S. Appl. No. 15/450,624.
Fukumoto et al., "Whisper: A Wristwatch Style Wearable Headset," CHI 99, May 1999, pp. 112-119.
Fukumoto et al., "Body Coupled FingeRing Wireless Wearable Keyboard," CHI 97, Mar. 1997, pp. 147-154.
Matsushita et al., "Wearable Key Device for Personalizing Nearby Environment, Proceedings of the Fourth International Symposium on Wearable Computers" (ISWC'00), Feb. 2000, pp. 1-8.
U.S. Office Action dated Apr. 5, 2018 in U.S. Appl. No. 15/250,375.
U.S. Office Action dated Mar. 22, 2018 in U.S. Appl. No. 15/450,624.

\* cited by examiner

MEASURING MUSCLE EXERTION USING BONE CONDUCTION

BACKGROUND

Through the use of bone conduction techniques, transducers, such as contact microphones, can send vibration signals through a human body, and more particularly, through one or more bones of the human body. The vibration signals after propagating through the bone(s) of the human body then can be used for numerous applications.

SUMMARY

Concepts and technologies are disclosed herein for measuring user exertion via bone conduction. According to one aspect, a device can generate a measurement signal. The device can cause a transducer to transmit the measurement signal through a body of a user. The device can receive, via the transducer, a modified measurement signal. The modified measurement signal can include the measurement signal as modified by the body of the user. The device can compare the modified measurement signal to a modified baseline signal. The device can determine, based on this comparison, a level of exertion experienced by the user.

In some embodiments, the device can instruct the user to relax one or more muscles. The device can then generate a baseline signal and cause the transducer to transmit the baseline signal through the body of the user. The device can receive, via the transducer, the modified baseline signal. The modified baseline signal can include the baseline signal as modified by the body of the user.

In some embodiments, the device can provide the level of exertion experienced by the user to an application. The device can execute the application to utilize the level of physical exertion experienced by the user.

In some embodiments, the level of exertion experienced by the user can be expressed in muscle exertion data that specifies how contracted one or more muscles of the body of the user are during a muscle activity. The muscle exertion data can be stored locally on the device. Alternatively or additionally, the muscle exertion data can be stored by a service that is accessible by the device via a network to which the device is connected.

It should be appreciated that the above-described subject matter may be implemented as a computer-controlled apparatus, a computer process, a computing system, or as an article of manufacture such as a computer-readable storage medium. These and various other features will be apparent from a reading of the following Detailed Description and a review of the associated drawings.

This Summary is provided to introduce a selection of concepts in a simplified form that are further described below in the Detailed Description. This Summary is not intended to identify key features or essential features of the claimed subject matter, nor is it intended that this Summary be used to limit the scope of the claimed subject matter. Furthermore, the claimed subject matter is not limited to implementations that solve any or all disadvantages noted in any part of this disclosure.

DETAILED DESCRIPTION

Figure 1:
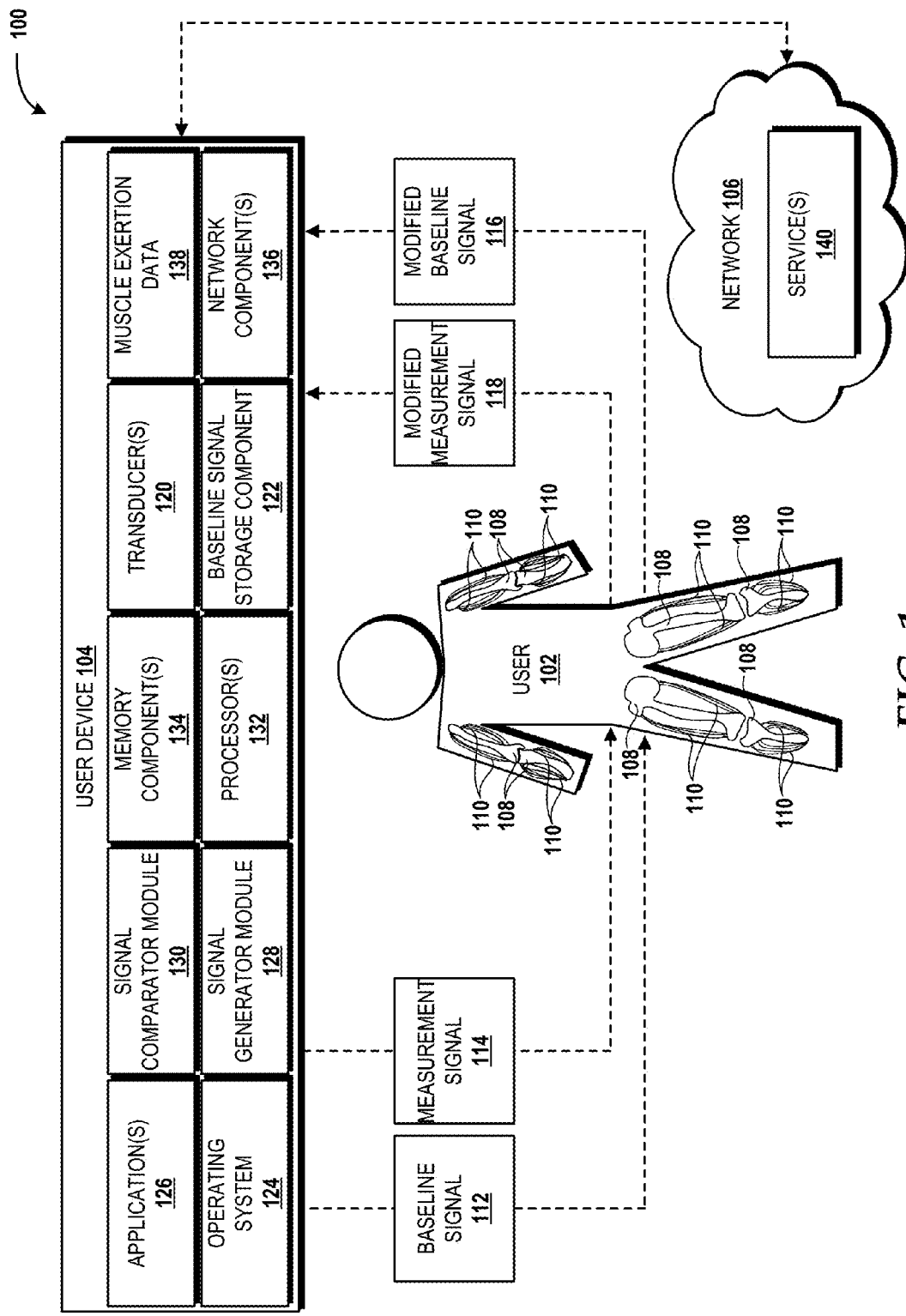
FIG. 1 is a block diagram illustrating aspects of an illustrative operating environment for various concepts disclosed herein.

Bone conduction is a developing communication technology with numerous potential applications. The nature of this technology is such that new functionality beyond communication can be added by observing changes in a received signal as the condition of a user changes. The concepts and technologies disclosed herein can utilize an observed change in a received bone conduction signal relative to a baseline reference signal to determine levels of exertion exhibited by a given user. A bone conduction signal sent through at least a portion of the user's body, and more particularly one or more bones of the user's body, while the user is relaxed will undergo certain changes. The same bone conduction signal sent through the same portion of the user's body while muscles within the portion of the user's body are contracted will exhibit changes that differ from those observed while muscles within the portion of the user's body are relaxed. This variation can be used to indirectly observe the state of the user's body/muscles along the signal path to determine when muscles within the signal path are contracted or relaxed. Furthermore, the concepts and technologies disclosed herein can discern levels within a range between relaxed muscles and fully contracted muscles indicative of varying levels of exertion. The concepts and disclosure disclosed herein can be utilized in several potential applications, some of which will be described herein.

While the subject matter described herein may be presented, at times, in the general context of program modules that execute in conjunction with the execution of an operating system and application programs on a computer system, those skilled in the art will recognize that other implementations may be performed in combination with other types of program modules. Generally, program modules include routines, programs, components, data structures, computer-executable instructions, and/or other types of structures that perform particular tasks or implement particular abstract data types. Moreover, those skilled in the art will appreciate that the subject matter described herein may be practiced with other computer system configurations, including hand-held devices, mobile devices, wireless devices, multiprocessor systems, distributed computing systems, microprocessor-based or programmable consumer electronics, minicomputers, mainframe computers, routers, switches, other computing devices described herein, and the like.

In the following detailed description, references are made to the accompanying drawings that form a part hereof, and in which are shown by way of illustration specific embodiments or examples. Referring now to the drawings, in which like numerals represent like elements throughout the several figures, example aspects of measuring muscle exertion using bone conduction will be presented.

Referring now to FIG. 1, aspects of an operating environment 100 in which various embodiments of the concepts and technologies presented herein may be implemented will be described. The operating environment 100 includes a user 102, a user device 104, and a network 106. The user 102 has a plurality of bones 108 ("bones 108") through which one or more signals may propagate, a process referred to herein as "bone conduction." The user 102 also has a plurality of muscles 110 ("muscles 110"). As the user 102 moves, one or more of the muscles 110 contract. The contraction of one or more of the muscles 110 can affect the propagation of one or more signals through the user's 102 body. It should be understood that a portion of a given bone conduction signal may propagate through other parts of the user's 102 body, such as fat, organ tissue, blood vessels, skin, and/or other tissue in addition to one or more of the bones 108.

A baseline bone conduction signal ("baseline signal 112") sent through one or more of the bones 108 within a portion the user's 102 body while the muscles 110 in the portion are relaxed will undergo changes that are different from a measurement bone conduction signal ("measurement signal" 114), having the same signal characteristics (e.g., phase, amplitude, and frequency) as the baseline signal 112, sent through the portion of user's 102 body while the muscles 110 in the portion are at least partially contracted. The changes observed between a modified baseline signal 116 (i.e., the baseline signal 112 after propagating through the user's 102 body) and a modified measurement signal 118 (i.e., the measurement signal 114 after propagating through the user's 102 body) can be used to indirectly observe the state of one or more of the muscles 110 along a signal path to determine when the muscle(s) 110 within the signal path are contracted or relaxed. Furthermore, a range between relaxed muscles and fully contracted muscles can be associated with varying levels of exertion, which may be utilized in several potential applications.

The user device 104 can be a smartphone, feature phone, personal digital assistant ("PDA"), tablet device, laptop computer, desktop computer, server computer, video game system, handheld video game system, media player, set-top box, vehicle computing system, smart watch, personal tracker or safety device, dumbbell or other fitness equipment, other computing device, a combination thereof, or the like. It should be understood that the functionality of the user device 104 can be provided by a single device, by two or more similar devices, and/or by two or more dissimilar devices.

In the illustrated embodiment, the user device 104 can utilize one or more transducers 120 to transmit vibration signals, such as the baseline signal 112 and the measurement signal 114. The transducer(s) 120, in some embodiments, are piezoelectric transducers, such as contact microphones or other electro-acoustic transducers. The transducer(s) 120 can be built-in to the user device 104 as shown, although other implementations where the transducers 120 are attached to or external to and in communication with the user device 104 are contemplated. As such, the illustrated configuration of the transducer(s) 120 should not be construed as being limiting in any way.

The baseline signal 112 and the measurement signal 114 each can be any signal that is capable of propagating through the user 102 via at least one or more of the bones 108. The baseline signal 112 and the measurement signal 114 can be generated to have any frequency, amplitude, and/or phase characteristics suitable for transmission through the user's 102 body. In some embodiments, the baseline signal 112 and/or the measurement signal 114 are generated after a setup process during which the user device 104, via the transducer(s) 120, transmits one or more signals through the user's 102 body in order to determine signal characteristics that are suitable for transmission through the user's 102 body.

In addition to the transducer(s) 120, the illustrated user device 104 includes a baseline signal storage component 122, an operating system 124, one or more applications 126, a signal generator module 128, a signal comparator module 130, one or more processor(s) 132, one or more memory components 134, one or more network components 136, and muscle exertion data 138. The baseline signal storage component 122 can be any memory component of the user device 104 or a portion of any memory component that can store, for example, the baseline signal 112 and the modified baseline signal 116. In some embodiments, the baseline signal storage component 122 stores multiple baseline signals.

The operating system 124 is a program for controlling the operation of the user device 104. In some embodiments, the operating system 124 includes the signal generator module 128 and/or the signal comparator module 130, both of which are described in greater detail below. The operating system 124 can be executed by the processor(s) 132 to cause the user device 104 to perform various operations. The operating system 124 can include a member of the SYMBIAN OS family of operating systems from SYMBIAN LIMITED, a member of the WINDOWS MOBILE OS and/or WINDOWS PHONE OS families of operating systems from MICROSOFT CORPORATION, a member of the PALM WEBOS family of operating systems from HEWLETT PACKARD CORPORATION, a member of the BLACKBERRY OS family of operating systems from RESEARCH IN MOTION LIMITED, a member of the IOS family of operating systems from APPLE INC., a member of the ANDROID OS family of operating systems from GOOGLE INC., and/or other operating systems. These operating systems are merely illustrative of some contemplated operating systems that may be used in accordance with various embodiments of the concepts and technologies described herein and therefore should not be construed as being limiting in any way.

The user device 104 can utilize the processor(s) 132 to execute the application(s) 126. The application(s) 126 can include, but are not limited to, fitness applications, productivity applications, entertainment applications, video applications, music applications, video game applications, camera applications, messaging applications, social network applications, enterprise applications, map applications, security applications, presence applications, visual voice mail applications, text-to-speech applications, speech-to-text applications, email applications, calendar applications, camera applications, web browser applications, combinations thereof, and the like. The application(s) 126 can execute on top of the operating system 124. The application(s) 126 can utilize the muscle exertion data 138 determined based upon a comparison, for example, of the modified baseline signal 116 to the modified measurement signal 118 to perform operations.

In some implementations, the application(s) 126 include a fitness training application that utilizes the muscle exertion data 138 to provide objective measurement of physical exertion experienced by the user 102. The muscle exertion data 138 can be provided in real-time or near real-time to establish adaptive training to maximize training results and to prevent injury. An observed exertion along with the body weight of the user 102 and the amount of weight lifted/moved to achieve the observed exertion can be incorporated, by the fitness training application, into a training model that can be modified over time as the user 102 progresses through an exercise program to help the user 102 improve his or her performance and to track his or her progress.

Activities that involve physical exertion put a strain on the muscles and ligaments involved. This strain causes these muscles to grow enabling greater output (e.g., lifting more weight). Unfortunately, poor form and a lack of focus on supporting muscles can lead to asymmetric development. As the output increases (e.g., lifting more weight) the strain on these muscles increases which is fine for the muscles in focus, but eventually the supporting muscles and ligaments that do not receive the same attention cannot support the load and fail. A common example of this type of failure is a torn rotator cuff. The muscle exertion data 138 obtained through the concepts and technologies disclosed herein can be used to prevent asymmetric exertion and resulting asymmetric muscle development, as well as to prevent serious injuries that often result. By comparing the muscle exertion data 138 across different muscle groups and parts of the user's 102 body, asymmetrical growth may be identified over time and recorded by the fitness training application.

The muscle exertion data 138 can be used in a comparison of measurements for similar activities and aligning the muscle exertion data 138 with other self-tracking data, including, but not limited to, sleep data and diet data, which can be utilized by the fitness training application to optimize the user's 102 performance. One of the problems with current self-tracking applications is an inability to measure certain aspects of daily life. Being able to accomplish a certain activity (e.g., run a mile or lift a certain amount of weight) does not include objective data regarding how difficult the activity was to accomplish for an individual. Since there is no measure of physical exertion, optimizing a workout or training regimen becomes nearly impossible. In other words, an individual cannot improve what he or she cannot measure. Those skilled in the art will appreciate the applicability of the muscle exertion data 138 to various other aspects of exercise, and as such, the forgoing examples should not be construed as being limiting in any way.

In some implementations, the application(s) 126 include a workplace safety application that can utilize the muscle exertion data 138 to monitor for overexertion by the user 102 during work-related tasks such as lifting and carrying objects. Similar functionality may be applied to overexertion and injury prevention outside of the workplace, such as for senior or disabled individuals in their daily activities.

In some implementations, the application(s) 126 include a physical habit monitoring application that can monitor habits related to, for example, standing and/or sitting posture, walking gait, and the like, and can provide insight regarding how poor habits can be corrected to prevent or at least mitigate long-term damage.

In some implementations, the application(s) 126 include a gaming application. The muscle exertion data 138 can be used to track user exertion during gameplay. The muscle exertion data 138 can be used to suggest to the user 102 that he or she discontinues playing. The muscle exertion data 138 can be used to modify a game character's behavior, such as to exhibit visual signs of being tired. Those skilled in the art will appreciate the applicability of the muscle exertion data 138 to various other aspects of gaming, and as such, the forgoing examples should not be construed as being limiting in any way.

In some implementations, the muscle exertion data 138 can be used to enhance, expand, and/or diversify the concepts and technologies disclosed in U.S. patent application Ser. No. 14/065,663 filed Oct. 29, 2013 and assigned to the Assignee of this application, which is hereby incorporated by reference in its entirety. For example, body position based on bone conduction signaling as described in the aforementioned U.S. Patent Application can be made more accurate by incorporating observations of muscle engagement as reflected in the muscle exertion data 138. The presence or absence of significant engagement of muscles within different portions of the user's 102 body may help determine mental and emotional state (e.g. exertion detected—clenched fists related to anger or aggression versus little or no exertion detected—closed fists related to cold temperature, grasping small objects, or similar).

In some implementations, the muscle exertion data 138 can be enhance, expand, and/or diversify the concepts and technologies disclosed in U.S. patent application Ser. No. 14/072,126 filed Nov. 5, 2013 and assigned to the Assignee of this application, which is hereby incorporated by reference in its entirety. Gesture controls as described in the aforementioned U.S. Patent Application can be enhanced and/or diversified by incorporating the muscle exertion data 138 into the control. For example, rather than having open hand versus a closed hand for on and off gestures, respectively, additional functionality can be included by incorporating the exertion associated with closing the hand. Considering the types of systems that might be controlled using gestures, any aspects of these systems with options along a spectrum (e.g., volume, brightness, contrast, and the like) rather than discrete values might be controlled using exertion tracking as well as gesture detection.

The operating system 124, the application(s) 126, the signal generator module 128, the signal comparator module 130, and/or muscle exertion data 138 can be stored in the memory component(s) 134. The memory component(s) 134 can include any computer storage medium, including, for example, volatile and non-volatile, removable and non-removable media implemented in any method or technology for storage of information such as computer-readable instructions, one or more data structures, one or more program modules (e.g., the signal generator module 128 and/or the signal comparator module 130), one or more operating systems (e.g., the operating system 124), one or more applications (e.g., the application(s) 126), and/or other data (e.g., the muscle exertion data 138. More particularly, the memory component(s) 134 can include, but are not limited to, random access memory ("RAM"), read-only memory ("ROM"), Erasable Programmable ROM ("EPROM"), Electrically Erasable Programmable ROM ("EEPROM"), flash memory or other solid state memory technology, CD-ROM, digital versatile disks ("DVD"), or other optical storage, magnetic cassettes, magnetic tape, magnetic disk storage or other magnetic storage devices, or any other medium which can be used to store the desired information and which can be accessed by the user device 104. In the claims, the phrase "computer storage medium" and variations thereof does not include waves or signals per se and/or communication media.

The signal generator module 128 can be executed by the processor(s) 132 to generate the baseline signal 112, the measurement signal 114, and potentially other signals used to measure physical exertion experienced by one or more of the muscles 110 of the user 102. The signal generator module 128, in some embodiments, is included in the operating system 124 and is accessible by one or more applications, such as the application(s) 126, to cause the signal generator module 128 to generate one or more signals, such as the baseline signal 112 and the measurement signal 114. In some other embodiments, the signal generator module 128 is included in the application(s) 126 or is provided as a stand-alone program module.

The signal comparator module 130 can be executed by the processor(s) 132 to compare the modified baseline signal 116 that is stored in the baseline signal storage component 122 to the modified measurement signal 118 to determine the muscle exertion data 138 indicative of a level of exertion experience by one or more of the muscles 110 of the user 102. The signal comparator module 130, in some embodiments, is included in the operating system 124 and is accessible by one or more applications, such as the application(s) 126, to cause the signal comparator module 130 to compare the modified baseline signal 116 that is stored in the baseline signal storage component 122 to the modified measurement signal 118. In some other embodiments, the signal comparator module 130 is included in the application(s) 126 or is provided as a stand-alone program module.

In the illustrated example, the user device 104 is in communication with the network 106 via the network component(s) 136. The network 106, in some embodiments, can be or can include one or more wireless personal area networks ("WPANs"), one or more wireless local area networks ("WLANs"), one or more wireless wide area networks ("WWANS"), one or more wireless metropolitan area networks ("WMANs"), one or more campus area networks ("CANs"), and/or one or more packet data networks, such as the internet or a portion thereof The network 106 may use any wireless communications technology or combination of wireless communications technologies, some examples of which include, but are not limited to, BLUETOOTH, ZIGBEE, WI-FI, WI-FI peer-to-peer, Global System for Mobile communications ("GSM"), Code Division Multiple Access ("CDMA") ONE, CDMA2000, Universal Mobile Telecommunications System ("UMTS"), Long-Term Evolution ("LTE"), Worldwide Interoperability for Microwave Access ("WiMAX"), other Institute of Electrical and Electronics Engineers ("IEEE") 802.XX technologies, and the like.

The network 106 embodied, at least in part, as a WWAN may operate using various channel access methods (which may or may not be used by the aforementioned technologies), including, but not limited to, Time Division Multiple Access ("TDMA"), Frequency Division Multiple Access ("FDMA"), CDMA, wideband CDMA ("W-CDMA"), Orthogonal Frequency Division Multiplexing ("OFDM"), Single-Carrier FDMA ("SC-FDMA"), Space Division Multiple Access ("SDMA"), and the like. Data may be exchanged via the communications network using cellular data technologies such as, but not limited to, General Packet Radio Service ("GPRS"), Enhanced Data rates for Global Evolution ("EDGE"), the High-Speed Packet Access ("HSPA") protocol family including High-Speed Downlink Packet Access ("HSDPA"), Enhanced Uplink ("EUL") or otherwise termed High-Speed Uplink Packet Access ("HSUPA"), Evolved HSPA ("HSPA+"), LTE, and/or various other current and future wireless data access technologies.

The network component(s) 136 can be or can include one or more transceivers. The transceiver(s), if included, can be configured to communicate over the same and/or different wireless technology standards. For example, in some embodiments, the transceiver(s) may be configured to communicate using GSM, CDMA, CDMAONE, CDMA2000, LTE, and various other 2G, 2.5G, 3G, 4G, and greater generation technology standards. Moreover, the transceiver(s) may facilitate communications over various channel access methods (which may or may not be used by the aforementioned standards) including, but not limited to, TDMA, FDMA, W-CDMA, OFDM, SDMA, and the like.

The network component(s) 136 may facilitate data communications using GPRS, EDGE, the HSPA protocol family, including HSDPA, EUL or otherwise termed HSUPA, HSPA+, and various other current and future wireless data access standards. The network component(s) 136 may include one or more transceivers for supporting other types and/or standards of communications, such as, for example, WI-FI, WIMAX, BLUETOOTH, infrared, infrared data association ("IRDA"), near-field communications ("NFC"), ZIGBEE, other RF technologies, combinations thereof, and the like.

The network 106 can provide the user device 104 access to one or more services 140. The service(s) 140 can be any service(s) that is accessible via a network connection. For example, the service(s) 140 can be or can include a voice call service, a voice over internet protocol ("VoIP") service, a voice over LTE ("VoLTE") service, a video call service, a media streaming service (e.g., a music or video service), a media download service, a web service, a local service (e.g., a local storage service), a data storage service, a television service, any combination thereof, and the like. In some embodiments, the service 140 includes a muscle exertion data storage service that stores at least a portion of the muscle exertion data 138. Other services may provide functionality the same as or similar to the operating system 124, the application(s) 126, the signal generator module 128, the signal comparator module 130, the baseline signal storage component 122, and/or other functionality described herein.

FIG. 1 illustrates one user 102, one user device 104, one network 106, one baseline signal 112, one measurement signal 114, one modified baseline signal 116, one modified measurement signal 118, one baseline signal storage component 122, one operating system 124, one signal generator module 128, and one signal comparator module 130. It should be understood, however, that various implementations of the operating environment 100 can include multiple users 102, multiple user devices 104, multiple networks 106, multiple baseline signals 112, multiple measurement signals 114, multiple modified baseline signals 116, multiple modified measurement signals 118, multiple baseline signal storage components 122, multiple operating systems 124, multiple signal generator modules 128, and/or multiple signal comparator modules 130. As such, the illustrated embodiment should be understood as being illustrative, and should not be construed as being limiting in any way.

Figure 2:
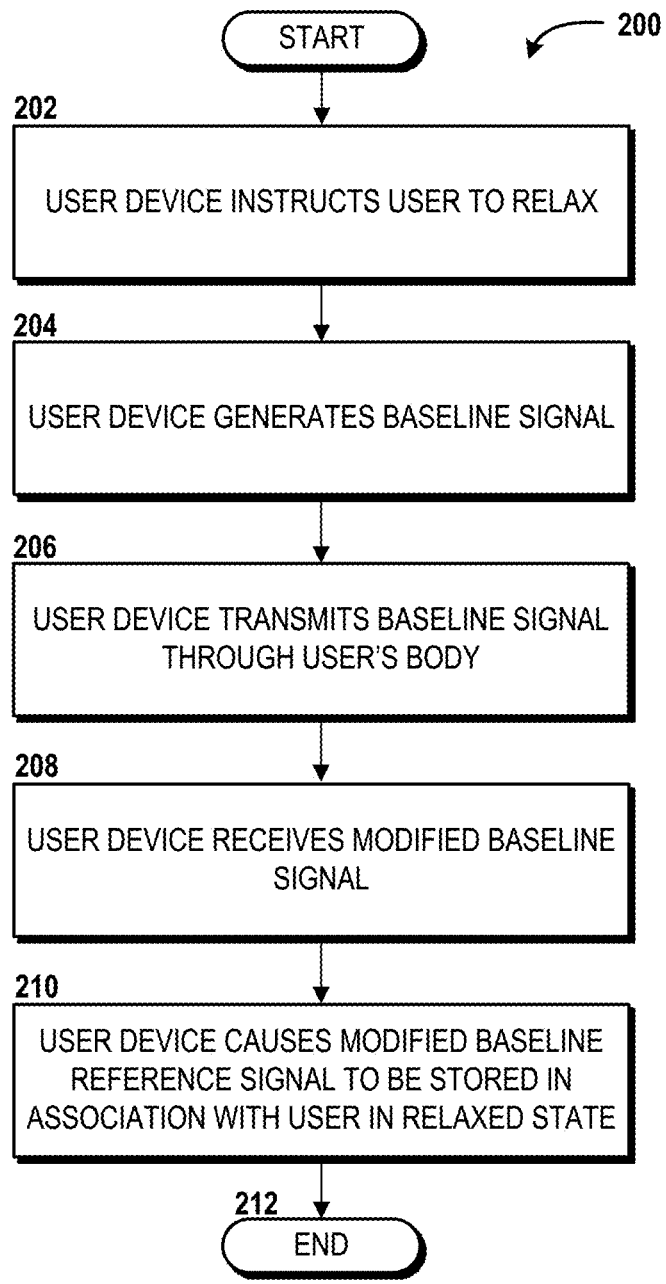
FIG. 2 is a flow diagram illustrating aspects of a method for establishing a baseline for use in measuring physical exertion by a user, according to an illustrative embodiment.

Turning now to FIG. 2, aspects of a method 200 for establishing a baseline for use in measuring physical exertion by the user 102 will be described, according to an illustrative embodiment. It should be understood that the operations of the methods are not necessarily presented in any particular order and that performance of some or all of the operations in an alternative order(s) is possible and is contemplated. The operations have been presented in the demonstrated order for ease of description and illustration. Operations may be added, omitted, and/or performed simultaneously, without departing from the scope of the concepts and technologies disclosed herein.

It also should be understood that the methods disclosed herein can be ended at any time and need not be performed in their respective entireties. Some or all operations of the methods, and/or substantially equivalent operations, can be performed by execution of computer-readable instructions included on a computer storage media, as defined herein. The term "computer-readable instructions," and variants thereof, as used herein, is used expansively to include routines, applications, application modules, program modules, programs, components, data structures, algorithms, and the like. Computer-readable instructions can be implemented on various system configurations including the user device 104, single-processor or multiprocessor systems, minicomputers, mainframe computers, personal computers, hand-held computing devices, microprocessor-based, programmable consumer electronics, other devices and systems disclosed herein, combinations thereof, and the like.

Thus, it should be appreciated that the logical operations described herein are implemented (1) as a sequence of computer implemented acts or program modules running on a computing system and/or (2) as interconnected machine logic circuits or circuit modules within the computing system. The implementation is a matter of choice dependent on the performance and other requirements of the computing system. Accordingly, the logical operations described herein are referred to variously as states, operations, structural devices, acts, or modules. These states, operations, structural devices, acts, and modules may be implemented in software, in firmware, in special purpose digital logic, and any combination thereof. As used herein, the phrase "cause a processor to perform operations" and variants thereof refers to causing one or more processors, such as the processor(s) 132, or one or more processors of another device disclosed herein, or another system disclosed herein, to perform one or more operations and/or causing the processor to direct other components of the computing system or device to perform one or more of the operations.

For purposes of illustrating and describing some of the concepts of the present disclosure, the methods disclosed herein are described as being performed, at least in part, by the user device 104 via execution, by the processor(s) 132, of one or more software modules and/or software applications, such as, for example, the operating system 124, the application(s) 126, the signal comparator module 130, and/or the signal generator module 128. It should be understood that additional and/or alternative devices and/or network nodes can provide the functionality described herein via execution of one or more modules, applications, and/or other software. Thus, the illustrated embodiments are illustrative, and should not be viewed as being limiting in any way.

The method 200 will be described with reference to FIG. 2 and further reference to FIG. 1. The method 200 will be described in context of the user device 104 executing, by the processor(s) 132, instructions for a setup process during which a baseline for measuring physical exertion by the user 102 can be established. The instructions for the setup process may be provided as part of the operating system 124 and/or the application(s) 126. In some embodiments, the setup process is performed prior to each measurement session. In some other embodiments, the setup process is performed only once. In some other embodiments, the setup process is performed at the request of the user 102. In some other embodiments, the setup process is performed as-needed.

The method 200 begins at operation 202, where the user device 104 instructs the user 102 to relax his or her muscles 110. The user device 104 may instruct the user 102 to relax his or her muscles 110 via text and/or images on a display (best shown in FIG. 4), via sound emitted by a speaker (also best shown in FIG. 4), or both.

From operation 202, the method 200 proceeds to operation 204, where the user device 104 generates the baseline signal 112 via execution, by the processor(s) 132, of the signal generator module 128. From operation 204, the method 200 proceeds to operation 206, where the user device 104 transmits, via the transducer(s) 120, the baseline signal 112 through at least a portion of the user's 102 body.

From operation 206, the method 200 proceeds to operation 208, where the user device 104 receives, via the transducer(s) 120, the modified baseline signal 116 (i.e., the baseline signal 112 after propagating through at least the portion of the user's 102 body). From operation 208, the method 200 proceeds to operation 210, where the user device 104 causes the modified baseline signal 116 to be stored in the baseline signal storage component 122 in association with the user 102 being in a relaxed state.

From operation 210, the method 200 proceeds to operation 212. The method 200 ends at operation 212.

Figure 3:
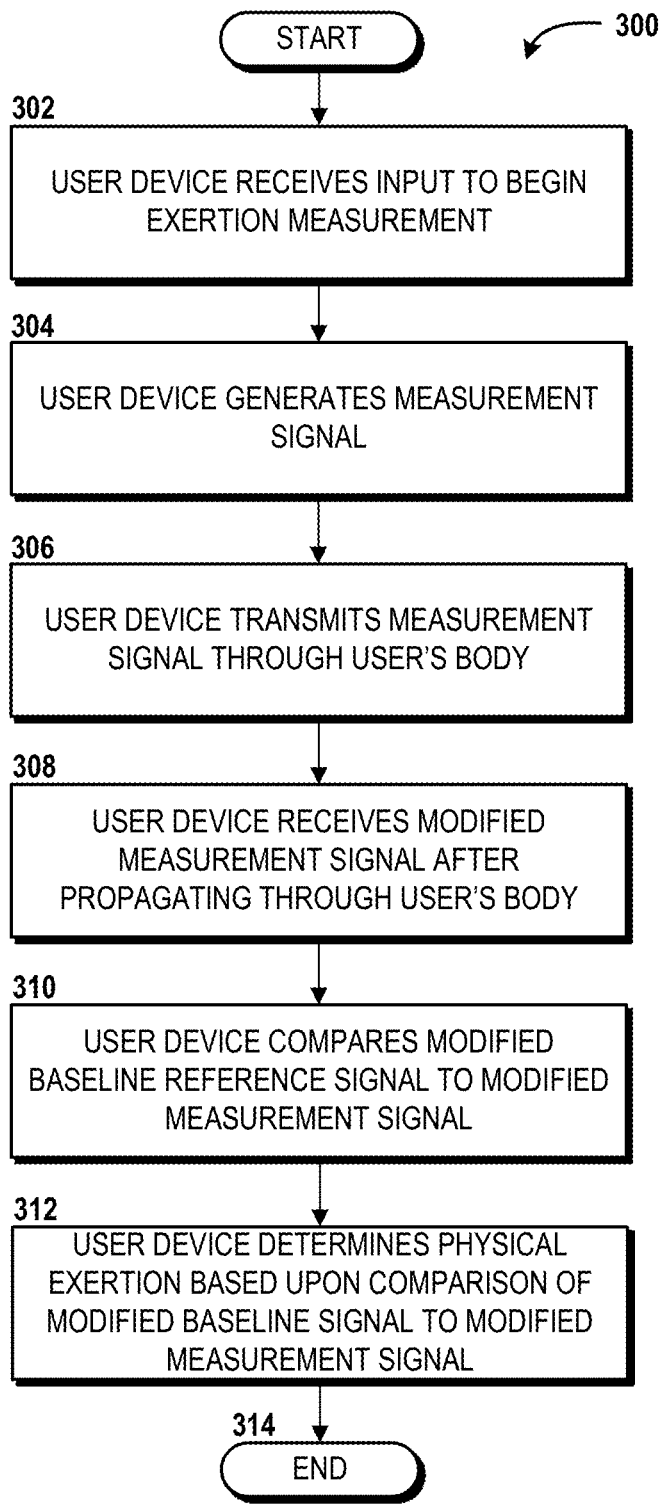
FIG. 3 is a flow diagram illustrating aspects of a method for using observed changes in a bone conduction signal, relative to a baseline, to determine changes in a level of physical exertion experienced by a user, according to an illustrative embodiment.

Turning now to FIG. 3, a method 300 for using observed changes in a bone conduction signal, relative to a baseline, to determine changes in a level of physical exertion experienced by the user 102 will be described, according to an illustrative embodiment. The method 300 will be described with reference to FIG. 3 and further reference to FIG. 1. The method 300 will be described in context of the user device 104 executing, by the processor(s) 132, instructions for an exertion determination process during which the physical exertion experienced by one or more of the muscles 110 of the user 102 can be measured. The instructions for the exertion determination process may be provided as part of the operating system 124 and/or the application(s) 126.

The method 300 begins and proceeds to operation 302, where the user device 104 receives an input instructing the user device 104 to begin exertion measurement. The input may be received from the user 102 or automatically via the operating system 124, and/or the application(s) 126. From operation 302, the method 300 proceeds to operation 304, where the user device 104 generates the measurement signal 114 via execution, by the processor(s) 132, of the signal generator module 128. As explained above, the measurement signal 114 can be generated to have the same phase, amplitude, and frequency characteristics as the baseline signal 112.

From operation 304, the method 300 proceeds to operation 306, where the user device 104 transmits, via the transducer(s) 120, the measurement signal 114 through at least a portion of the user's 102 body. In some embodiments, the user device 104 may prompt, via text, image, video, haptic feedback, and/or sound, the user to begin exertion (i.e., contraction of one or more of the muscles 110). From operation 306, the method 300 proceeds to operation 308, where the user device 104 receives, via the transducer(s) 120, the modified measurement signal 118 (i.e., the measurement signal 114 after propagating through at least the portion of the user's 102 body).

From operation 308, the method 300 proceeds to operation 310, where the user device 104 compares the modified baseline signal 116 previously stored in the baseline signal storage component 122 (FIG. 2; see operation 210 of the method 200) to the modified measurement signal 118 via execution, by the processor(s) 132, of the signal comparator module 130. From operation 310, the method 300 proceeds to operation 312, where the user device 104 determines the physical exertion experienced by one or more of the muscles 110 of the user 102 based upon the comparison, at operation 310, of the modified baseline signal 116 to the modified measurement 118.

Several differences may be discerned when the user 102 is exerting different muscles. For example, an increase in amplitude of the signal as well as a phase and frequency shift can be indicative of muscle exertion. Moreover, some frequencies may provide a better response with certain muscles, which allows exerted muscles to be isolated to determine the general area where the exertion was happening. Signal changes, in some implementations, are close to linear, so a normalization for the user 102 can allow for the detection of different levels of exertion.

From operation 312, the method 300 proceeds to operation 314. The method 300 ends at operation 314.

In some embodiments, relative exertion changes are tracked and compared to previous values. Observed minimums and maximums can be considered to be absolute minimums and maximums until new values are observed. In this manner, scaling can be as small or as large as needed. Moreover, this implementation enables different responses for different users as well as different systems/devices. Exertion value ranges, in some embodiments, are related to which activity is being performed.

Figure 4:
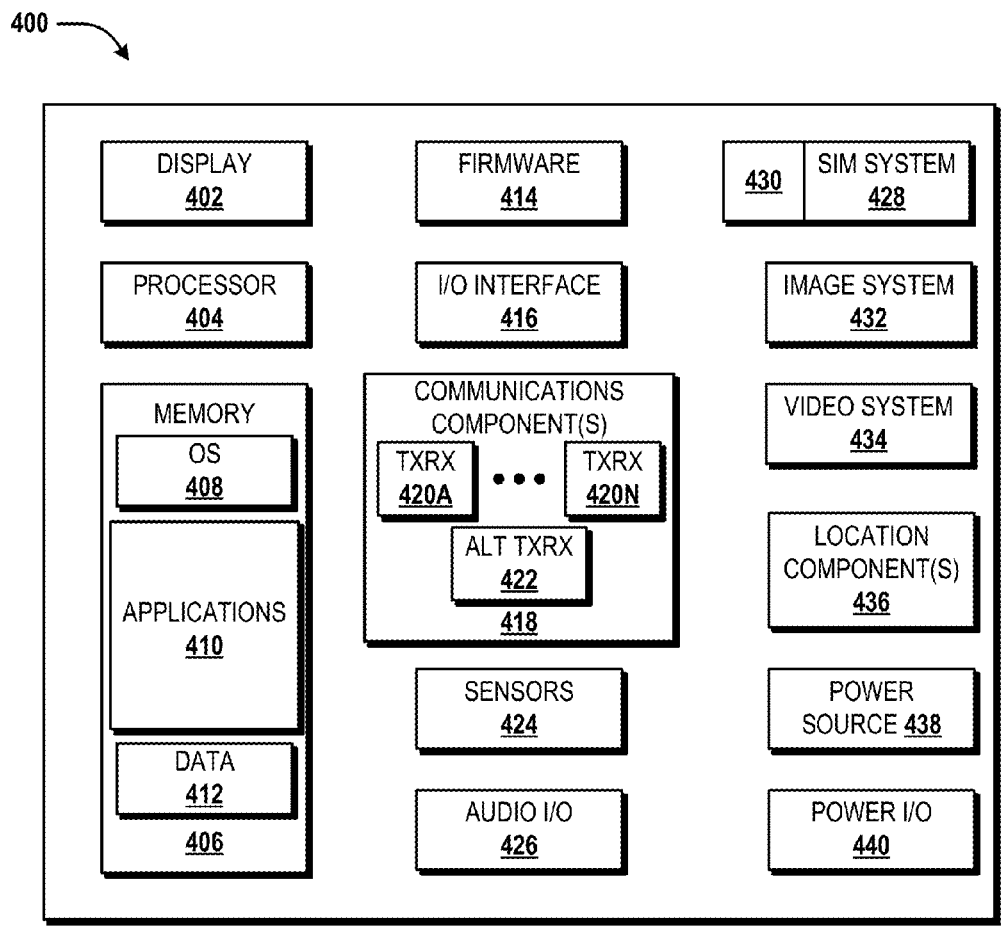
FIG. 4 is a block diagram illustrating an example mobile device capable of implementing aspects of the embodiments disclosed herein.

Turning now to FIG. 4, an illustrative mobile device 400 and components thereof will be described. In some embodiments, the user device 104 described above with reference to FIG. 1 can be configured as and/or can have an architecture similar or identical to the mobile device 400 described herein in FIG. 4. It should be understood, however, that the user device 104 may or may not include the functionality described herein with reference to FIG. 4. While connections are not shown between the various components illustrated in FIG. 4, it should be understood that some, none, or all of the components illustrated in FIG. 4 can be configured to interact with one other to carry out various device functions. In some embodiments, the components are arranged so as to communicate via one or more busses (not shown). Thus, it should be understood that FIG. 4 and the following description are intended to provide a general understanding of a suitable environment in which various aspects of embodiments can be implemented, and should not be construed as being limiting in any way.

As illustrated in FIG. 4, the mobile device 400 can include a display 402 for displaying data. According to various embodiments, the display 402 can be configured to display various graphical user interface ("GUI") elements, text, images, video, advertisements, prompts, virtual keypads and/or keyboards, messaging data, notification messages, metadata, internet content, device status, time, date, calendar data, device preferences, map and location data, combinations thereof, and the like. The mobile device 400 also can include a processor 404, such as the processor 132, and a memory or other data storage device ("memory") 406, such as the memory component 134. The processor 404 can be configured to process data and/or can execute computer-executable instructions stored in the memory 406. The computer-executable instructions executed by the processor 404 can include, for example, an operating system 408 (e.g., the operating system 124), one or more applications 410 (e.g., the application(s) 126, the signal generator module 128, and/or the signal comparator module 130), other computer-executable instructions stored in a memory 406, or the like. In some embodiments, the applications 410 also can include a UI application (not illustrated in FIG. 4).

The UI application can interface with the operating system 408 to facilitate user interaction with functionality and/or data stored at the mobile device 400 and/or stored elsewhere. In some embodiments, the operating system 408 can include a member of the SYMBIAN OS family of operating systems from SYMBIAN LIMITED, a member of the WINDOWS MOBILE OS and/or WINDOWS PHONE OS families of operating systems from MICROSOFT CORPORATION, a member of the PALM WEBOS family of operating systems from HEWLETT PACKARD CORPORATION, a member of the BLACKBERRY OS family of operating systems from RESEARCH IN MOTION LIMITED, a member of the IOS family of operating systems from APPLE INC., a member of the ANDROID OS family of operating systems from GOOGLE INC., and/or other operating systems. These operating systems are merely illustrative of some contemplated operating systems that may be used in accordance with various embodiments of the concepts and technologies described herein and therefore should not be construed as being limiting in any way.

The UI application can be executed by the processor 404 to aid a user in entering content, viewing account information, answering/initiating calls, entering/deleting data, entering and setting user IDs and passwords for device access, configuring settings, manipulating address book content and/or settings, multimode interaction, interacting with other applications 410, and otherwise facilitating user interaction with the operating system 408, the applications 410, and/or other types or instances of data 412 that can be stored at the mobile device 400. The data 412 can include, for example, the muscle exertion data 138, and/or data associated with applications or program modules. According to various embodiments, the data 412 can include, for example, presence applications, visual voice mail applications, messaging applications, text-to-speech and speech-to-text applications, add-ons, plug-ins, email applications, music applications, video applications, camera applications, location-based service applications, power conservation applications, game applications, productivity applications, entertainment applications, enterprise applications, combinations thereof, and the like. The applications 410, the data 412, and/or portions thereof can be stored in the memory 406 and/or in a firmware 414, and can be executed by the processor 404. The firmware 414 also can store code for execution during device power up and power down operations. It can be appreciated that the firmware 414 can be stored in a volatile or non-volatile data storage device including, but not limited to, the memory 406 and/or a portion thereof.

The mobile device 400 also can include an input/output ("I/O") interface 416. The I/O interface 416 can be configured to support the input/output of data such as location information, user information, organization information, presence status information, user IDs, passwords, and application initiation (start-up) requests. In some embodiments, the I/O interface 416 can include a hardwire connection such as USB port, a mini-USB port, a micro-USB port, an audio jack, a PS2 port, an IEEE 1344 ("FIREWIRE") port, a serial port, a parallel port, an Ethernet (RJ45) port, an RJ11 port, a proprietary port, combinations thereof, or the like. In some embodiments, the mobile device 400 can be configured to synchronize with another device to transfer content to and/or from the mobile device 400. In some embodiments, the mobile device 400 can be configured to receive updates to one or more of the applications 410 via the I/O interface 416, though this is not necessarily the case. In some embodiments, the I/O interface 416 accepts I/O devices such as keyboards, keypads, mice, interface tethers, printers, plotters, external storage, touch/multi-touch screens, touch pads, trackballs, joysticks, microphones, remote control devices, displays, projectors, medical equipment (e.g., stethoscopes, heart monitors, and other health metric monitors), modems, routers, external power sources, docking stations, combinations thereof, and the like. It should be appreciated that the I/O interface 416 may be used for communications between the mobile device 400 and a network device or local device.

The mobile device 400 also can include a communications component 418, such as the network component(s) 136. The communications component 418 can be configured to interface with the processor 404 to facilitate wired and/or wireless communications with one or more networks such as the network 106 described above. In some embodiments, other networks include networks that utilize non-cellular wireless technologies such as WI-FI or WIMAX. In some embodiments, the communications component 418 includes a multimode communications subsystem for facilitating communications via the cellular network and one or more other networks.

The communications component 418, in some embodiments, includes one or more transceivers. The one or more transceivers, if included, can be configured to communicate over the same and/or different wireless technology standards with respect to one another. For example, in some embodiments one or more of the transceivers of the communications component 418 may be configured to communicate using GSM, CDMA, CDMAONE, CDMA2000, LTE, and various other 2G, 2.5G, 3G, 4G, and greater generation technology standards. Moreover, the communications component 418 may facilitate communications over various channel access methods (which may or may not be used by the aforementioned standards) including, but not limited to, TDMA, FDMA, W-CDMA, OFDM, SDMA, and the like.

In addition, the communications component 418 may facilitate data communications using GPRS, EDGE, the HSPA protocol family, including HSDPA, EUL or otherwise termed HSUPA, HSPA+, and various other current and future wireless data access standards. In the illustrated embodiment, the communications component 418 can include a first transceiver ("TxRx") 420A that can operate in a first communications mode (e.g., GSM). The communications component 418 also can include an $N^{th}$ transceiver ("TxRx") 420N that can operate in a second communications mode relative to the first transceiver 420A (e.g., UMTS). While two transceivers 420A-N (hereinafter collectively and/or generically referred to as "transceivers 420") are shown in FIG. 4, it should be appreciated that less than two, two, and/or more than two transceivers 420 can be included in the communications component 418.

The communications component 418 also can include an alternative transceiver ("Alt TxRx") 422 for supporting other types and/or standards of communications. According to various contemplated embodiments, the alternative transceiver 422 can communicate using various communications technologies such as, for example, WI-FI, WIMAX, BLUETOOTH, infrared, IRDA, NFC, other RF technologies, combinations thereof, and the like.

In some embodiments, the communications component 418 also can facilitate reception from terrestrial radio networks, digital satellite radio networks, internet-based radio service networks, combinations thereof, and the like. The communications component 418 can process data from a network such as the internet, an intranet, a broadband network, a WI-FI hotspot, an Internet service provider ("ISP"), a digital subscriber line ("DSL") provider, a broadband provider, combinations thereof, or the like.

The mobile device 400 also can include one or more sensors 424. The sensors 424 can include temperature sensors, light sensors, air quality sensors, movement sensors, orientation sensors, noise sensors, proximity sensors, or the like. As such, it should be understood that the sensors 424 can include, but are not limited to, accelerometers, magnetometers, gyroscopes, infrared sensors, noise sensors, microphones, combinations thereof, or the like. Additionally, audio capabilities for the mobile device 400 may be provided by an audio I/O component 426. The audio I/O component 426 of the mobile device 400 can include one or more speakers for the output of audio signals, one or more microphones for the collection and/or input of audio signals, and/or other audio input and/or output devices.

The illustrated mobile device 400 also can include a subscriber identity module ("SIM") system 428. The SIM system 428 can include a universal SIM ("USIM"), a universal integrated circuit card ("UICC") and/or other identity devices. The SIM system 428 can include and/or can be connected to or inserted into an interface such as a slot interface 430. In some embodiments, the slot interface 430 can be configured to accept insertion of other identity cards or modules for accessing various types of networks. Additionally, or alternatively, the slot interface 430 can be configured to accept multiple subscriber identity cards. Because other devices and/or modules for identifying users and/or the mobile device 400 are contemplated, it should be understood that these embodiments are illustrative, and should not be construed as being limiting in any way.

The mobile device 400 also can include an image capture and processing system 432 ("image system"). The image system 432 can be configured to capture or otherwise obtain photos, videos, and/or other visual information. As such, the image system 432 can include cameras, lenses, charge-coupled devices ("CCDs"), combinations thereof, or the like. The mobile device 400 may also include a video system 434. The video system 434 can be configured to capture, process, record, modify, and/or store video content. Photos and videos obtained using the image system 432 and the video system 434, respectively, may be added as message content to an multimedia message service ("MMS") message, email message, and sent to another mobile device. The video and/or photo content also can be shared with other devices via various types of data transfers via wired and/or wireless communication devices as described herein.

The mobile device 400 also can include one or more location components 436. The location components 436 can be configured to send and/or receive signals to determine a geographic location of the mobile device 400. According to various embodiments, the location components 436 can send and/or receive signals from global positioning system ("GPS") devices, A-GPS devices, WI-FI/WIMAX and/or cellular network triangulation data, combinations thereof, and the like. The location component 436 also can be configured to communicate with the communications component 418 to retrieve triangulation data for determining a location of the mobile device 400. In some embodiments, the location component 436 can interface with cellular network nodes, telephone lines, satellites, location transmitters and/or beacons, wireless network transmitters and receivers, combinations thereof, and the like. In some embodiments, the location component 436 can include and/or can communicate with one or more of the sensors 424 such as a compass, an accelerometer, and/or a gyroscope to determine the orientation of the mobile device 400. Using the location component 436, the mobile device 400 can generate and/or receive data to identify its geographic location, or to transmit data used by other devices to determine the location of the mobile device 400. The location component 436 may include multiple components for determining the location and/or orientation of the mobile device 400.

The illustrated mobile device 400 also can include a power source 438. The power source 438 can include one or more batteries, power supplies, power cells, and/or other power subsystems including alternating current ("AC") and/or direct current ("DC") power devices. The power source 438 also can interface with an external power system or charging equipment via a power I/O component 440. Because the mobile device 400 can include additional and/or alternative components, the above embodiment should be understood as being illustrative of one possible operating environment for various embodiments of the concepts and technologies described herein. The described embodiment of the mobile device 400 is illustrative, and should not be construed as being limiting in any way.

Figure 5:
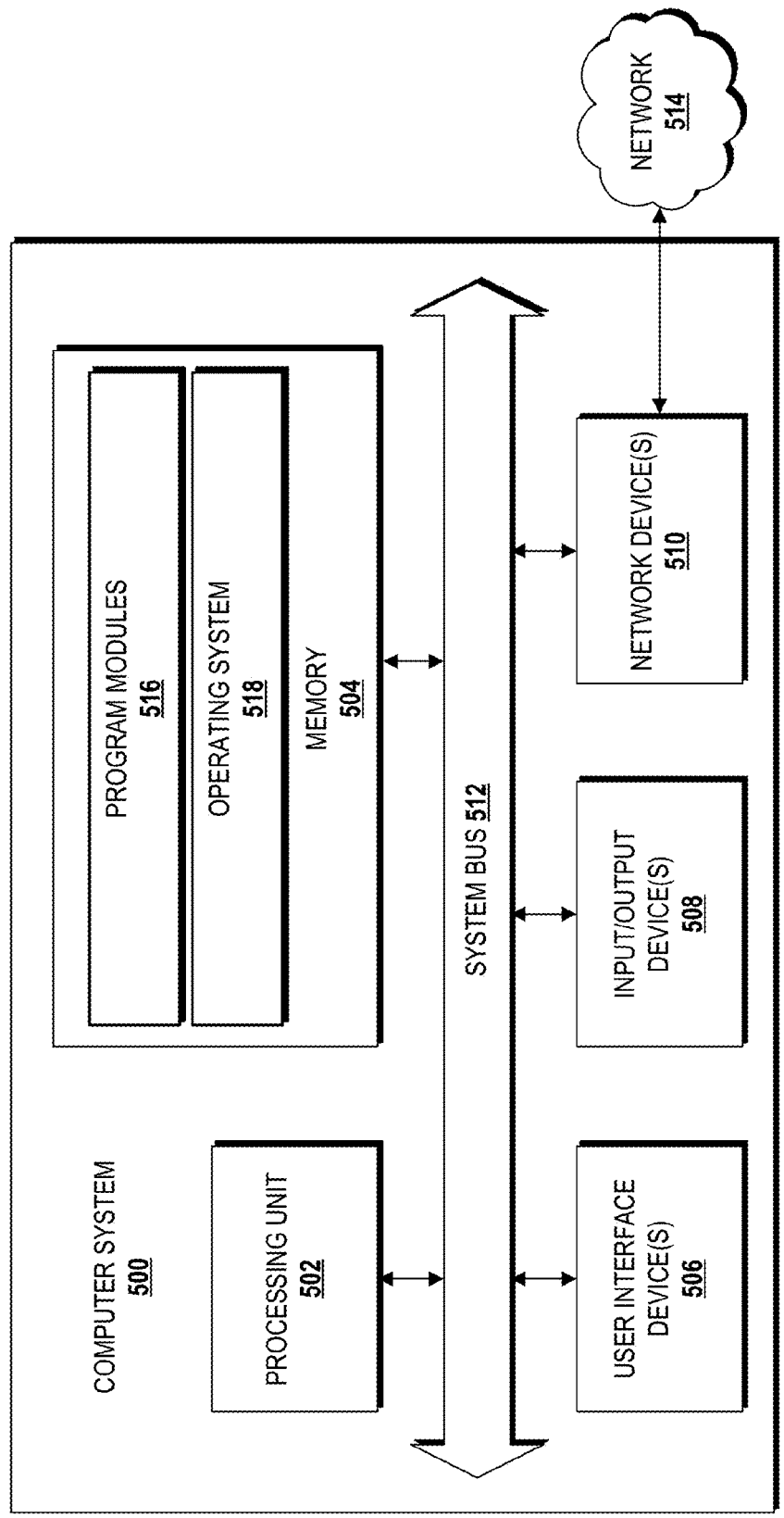
FIG. 5 is a block diagram illustrating an example computer system capable of implementing aspects of the embodiments presented herein.

FIG. 5 is a block diagram illustrating a computer system 500 configured to provide the functionality in accordance with various embodiments of the concepts and technologies disclosed herein. In some implementations, the user device 104 and/or one or more servers configured to provide at least a portion of the service(s) 140 utilize an architecture that is the same as or similar to the architecture of the computer system 500. It should be understood, however, that modification to the architecture may be made to facilitate certain interactions among elements described herein.

The computer system 500 includes a processing unit 502, a memory 504, one or more user interface devices 506, one or more input/output ("I/O") devices 508, and one or more network devices 510, each of which is operatively connected to a system bus 512. The bus 512 enables bi-directional communication between the processing unit 502, the memory 504, the user interface devices 506, the I/O devices 508, and the network devices 510.

The processing unit 502 may be a standard central processor that performs arithmetic and logical operations, a more specific purpose programmable logic controller ("PLC"), a programmable gate array, a system-on-a-chip, or other type of processor known to those skilled in the art and suitable for controlling the operation of the server computer. Processing units are generally known, and therefore are not described in further detail herein.

The memory 504 communicates with the processing unit 502 via the system bus 512. In some embodiments, the memory 504 is operatively connected to a memory controller (not shown) that enables communication with the processing unit 502 via the system bus 512. The memory 504 includes an operating system 518 and one or more program modules 516. The operating system 518 can include, but is not limited to, members of the WINDOWS, WINDOWS CE, and/or WINDOWS MOBILE families of operating systems from MICROSOFT CORPORATION, the LINUX family of operating systems, the SYMBIAN family of operating systems from SYMBIAN LIMITED, the BREW family of operating systems from QUALCOMM CORPORATION, the MAC OS, iOS, and/or LEOPARD families of operating systems from APPLE CORPORATION, the FREEBSD family of operating systems, the SOLARIS family of operating systems from ORACLE CORPORATION, other operating systems, and the like.

The program modules 516 may include various software and/or program modules to perform the various operations described herein. The program modules 516 and/or other programs can be embodied in computer-readable media containing instructions that, when executed by the processing unit 502. According to embodiments, the program modules 516 may be embodied in hardware, software, firmware, or any combination thereof. Although not shown in FIG. 5, it should be understood that the memory 504 also can be configured to data, if desired.

By way of example, and not limitation, computer-readable media may include any available computer storage media or communication media that can be accessed by the computer system 500. Communication media includes computer-readable instructions, data structures, program modules, or other data in a modulated data signal such as a carrier wave or other transport mechanism and includes any delivery media. The term "modulated data signal" means a signal that has one or more of its characteristics changed or set in a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

Computer storage media includes volatile and non-volatile, removable and non-removable media implemented in any method or technology for storage of information such as computer-readable instructions, data structures, program modules, or other data. Computer storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer system 500. In the claims, the phrase "computer storage medium" and variations thereof does not include waves or signals per se and/or communication media.

The user interface devices 506 may include one or more devices with which a user accesses the computer system 500. The user interface devices 506 may include, but are not limited to, computers, servers, personal digital assistants, cellular phones, or any suitable computing devices. The I/O devices 508 enable a user to interface with the program modules 516. In one embodiment, the I/O devices 508 are operatively connected to an I/O controller (not shown) that enables communication with the processing unit 502 via the system bus 512. The I/O devices 508 may include one or more input devices, such as, but not limited to, a keyboard, a mouse, or an electronic stylus. Further, the I/O devices 508 may include one or more output devices, such as, but not limited to, a display screen or a printer.

The network devices 510 enable the computer system 500 to communicate with other networks or remote systems via a network 514, such as the network 106. Examples of the network devices 510 include, but are not limited to, a modem, a radio frequency ("RF") or infrared ("IR") transceiver, a telephonic interface, a bridge, a router, or a network card. The network 514 may include a wireless network such as, but not limited to, a WLAN, a WWAN, a WPAN such as provided via BLUETOOTH technology, a WMAN such as a WiMAX network or metropolitan cellular network. Alternatively, the network 514 may be a wired network such as, but not limited to, a WAN, a wired LAN such as provided via Ethernet, a wired PAN, or a wired MAN.

Figure 6:
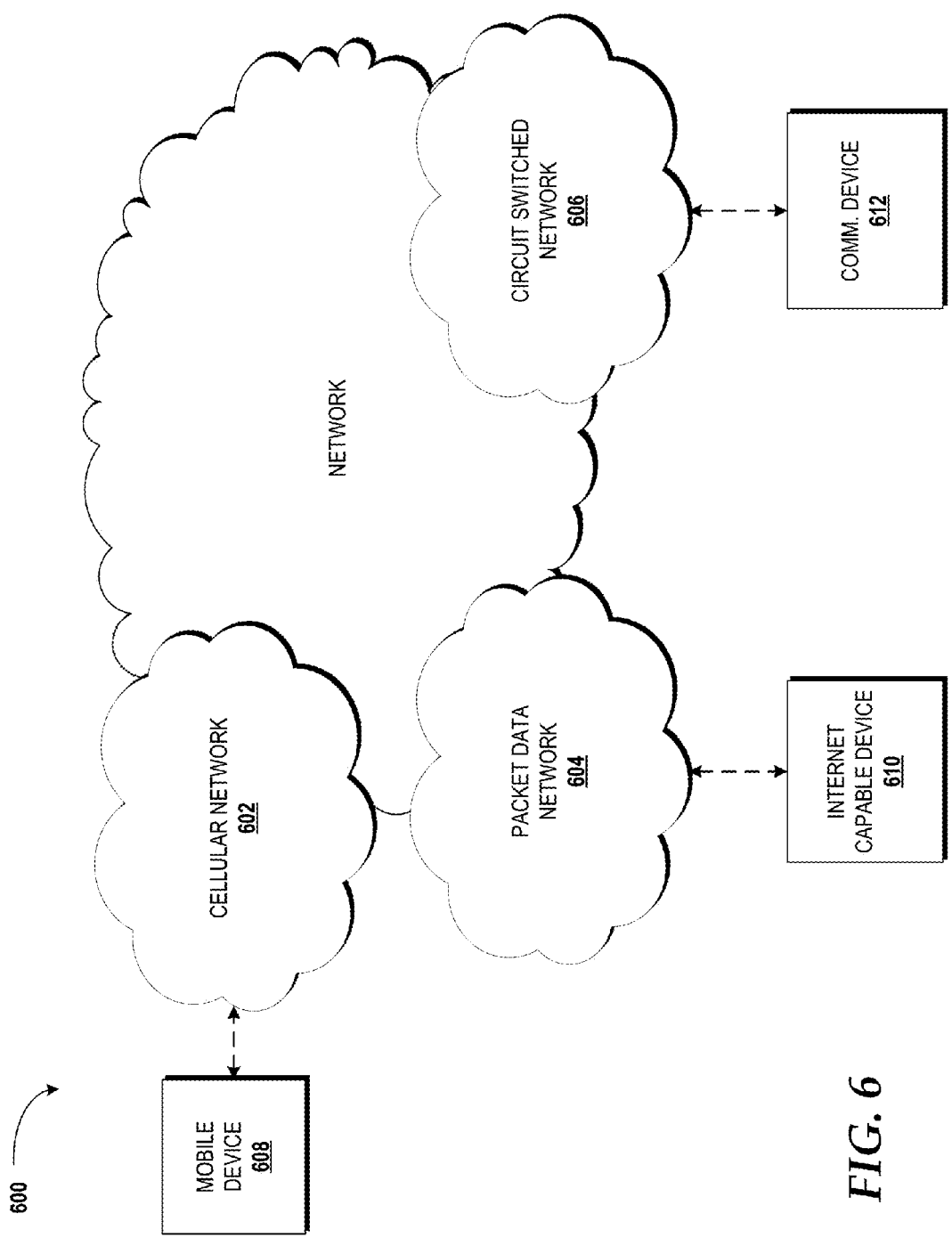
FIG. 6 schematically illustrates a network, according to an illustrative embodiment.

Turning now to FIG. 6, additional details of a network 600, such as the network 106, are illustrated, according to an illustrative embodiment. The network 600 includes a cellular network 602, a packet data network 604, for example, the internet, and a circuit switched network 606, for example, a publicly switched telephone network ("PSTN"). The cellular network 602 includes various components such as, but not limited to, base transceiver stations ("BTSs"), Node-B's or e-Node-B's, base station controllers ("BSCs"), radio network controllers ("RNCs"), mobile switching centers ("MSCs"), mobile management entities ("MMEs"), short message service centers ("SMSCs"), multimedia messaging service centers ("MMSCs"), home location registers ("HLRs"), home subscriber servers ("HSSs"), visitor location registers ("VLRs"), charging platforms, billing platforms, voicemail platforms, GPRS core network components, location service nodes, an IP Multimedia Subsystem ("IMS"), and the like. The cellular network 602 also includes radios and nodes for receiving and transmitting voice, data, and combinations thereof to and from radio transceivers, networks, the packet data network 604, and the circuit switched network 606.

A mobile communications device 608, such as, for example, a cellular telephone, a user equipment, a mobile terminal, a PDA, a laptop computer, a handheld computer, the user device 104, and combinations thereof, can be operatively connected to the cellular network 602. The cellular network 602 can be configured as a 2G GSM network and can provide data communications via GPRS and/or EDGE. Additionally, or alternatively, the cellular network 602 can be configured as a 3G UMTS network and can provide data communications via the HSPA protocol family, for example, HSDPA, EUL (also referred to as HSUPA), and HSPA+. The cellular network 602 also is compatible with 4G mobile communications standards such as LTE, or the like, as well as evolved and future mobile standards.

The packet data network 604 includes various devices, for example, servers, computers, databases, and other devices in communication with one another, as is generally known. The packet data network 604 devices are accessible via one or more network links. The servers often store various files that are provided to a requesting device such as, for example, a computer, a terminal, a smartphone, or the like. Typically, the requesting device includes software (a "browser") for executing a web page in a format readable by the browser or other software. Other files and/or data may be accessible via "links" in the retrieved files, as is generally known. In some embodiments, the packet data network 604 includes or is in communication with the Internet. The circuit switched network 606 includes various hardware and software for providing circuit switched communications. The circuit switched network 606 may include, or may be, what is often referred to as a plain old telephone system (POTS). The functionality of a circuit switched network 606 or other circuit-switched network are generally known and will not be described herein in detail.

The illustrated cellular network 602 is shown in communication with the packet data network 604 and a circuit switched network 606, though it should be appreciated that this is not necessarily the case. One or more Internet-capable devices 610, for example, the user device 104, a PC, a laptop, a portable device, or another suitable device, can communicate with one or more cellular networks 602, and devices connected thereto, through the packet data network 604. It also should be appreciated that the Internet-capable device 610 can communicate with the packet data network 604 through the circuit switched network 606, the cellular network 602, and/or via other networks (not illustrated).

As illustrated, a communications device 612, for example, a telephone, facsimile machine, modem, computer, the user device 104, or the like, can be in communication with the circuit switched network 606, and therethrough to the packet data network 604 and/or the cellular network 602. It should be appreciated that the communications device 612 can be an Internet-capable device, and can be substantially similar to the Internet-capable device 610. In the specification, the network 600 is used to refer broadly to any combination of the networks 602, 604, 606. It should be appreciated that substantially all of the functionality described with reference to the network 106 can be performed by the cellular network 602, the packet data network 604, and/or the circuit switched network 606, alone or in combination with other networks, network elements, and the like.

Based on the foregoing, it should be appreciated that concepts and technologies directed to measuring user exertion via bone conduction have been disclosed herein. Although the subject matter presented herein has been described in language specific to computer structural features, methodological and transformative acts, specific computing machinery, and computer-readable media, it is to be understood that the concepts and technologies disclosed herein are not necessarily limited to the specific features, acts, or media described herein. Rather, the specific features, acts and mediums are disclosed as example forms of implementing the concepts and technologies disclosed herein.

The subject matter described above is provided by way of illustration only and should not be construed as limiting. Various modifications and changes may be made to the subject matter described herein without following the example embodiments and applications illustrated and described, and without departing from the true spirit and scope of the embodiments of the concepts and technologies disclosed herein.

We claim:

1. A method comprising:

instructing, by a mobile device comprising a processor and an electro-acoustic transducer, a user to relax at least one muscle;

generating, by the mobile device, via execution of a signal generator module by the processor of the mobile device, a baseline bone conduction signal;

causing, by the mobile device, the electro-acoustic transducer to transmit the baseline bone conduction signal through at least one bone of a body of the user while the user relaxes the at least one muscle;

receiving, by the mobile device, via the electro-acoustic transducer, a modified baseline bone conduction signal, wherein the modified baseline bone conduction signal comprises the baseline bone conduction signal modified by the body of the user while the user relaxes the at least one muscle responsive to receiving instruction from the mobile device;

receiving, by the mobile device, an input instructing the mobile device to begin an exertion measurement to obtain muscle exertion data indicative of a level of exertion experienced by the at least one muscle;

in response to receiving the input instructing the mobile device to begin the exertion measurement, generating, by the mobile device, via execution of the signal generator module by the processor of the mobile device, a measurement bone conduction signal;

causing, by the mobile device, the electro-acoustic transducer to transmit the measurement bone conduction signal through the at least one bone of the body of the user while the user contracts the at least one muscle;

receiving, by the mobile device, via the electro-acoustic transducer, a modified measurement bone conduction signal, wherein the modified measurement bone conduction signal comprises the measurement bone conduction signal as modified by the body of the user while the user contracts the at least one muscle of the body of the user; and comparing, by the mobile device, via execution of a signal comparator module by the processor of the mobile device, the modified measurement bone conduction signal to the modified baseline bone conduction signal to obtain the muscle exertion data indicative of the level of exertion experienced by the at least one muscle.

2. The method of claim 1, further comprising:

providing, by the mobile device, the level of exertion experienced by the at least one muscle to an application; and executing, by the processor of the mobile device, the application to utilize the level of exertion to perform an operation.

3. The method of claim 1, further comprising causing, by the mobile device, the muscle exertion data to be stored.

4. The method of claim 3, wherein causing, by the mobile device, the muscle exertion data to be stored comprises causing, by the mobile device, the muscle exertion data to be stored in a memory component of the mobile device.

5. The method of claim 3, wherein causing, by the mobile device, the muscle exertion data to be stored comprises causing, by the mobile device, the muscle exertion data to be stored by a service that is accessible by the mobile device via a network to which the mobile device is connected.

6. A mobile device comprising:

an electro-acoustic transducer;

a processor; and a memory that stores computer-readable instructions that, when executed by the processor, cause the mobile device to perform operations comprising instructing a user to relax at least one muscle, generating a baseline bone conduction signal, causing the electro-acoustic transducer to transmit the baseline bone conduction signal through at least one bone of a body of the user while the user relaxes the at least one muscle, receiving, via the electro-acoustic transducer, a modified baseline bone conduction signal, wherein the modified baseline bone conduction signal comprises the baseline bone conduction signal modified by the body of the user while the user relaxes the at least one muscle responsive to receiving instruction from the mobile device, receiving an input instructing the mobile device to begin an exertion measurement to obtain muscle exertion data indicative of a level of exertion experienced by the at least one muscle, in response to receiving the input instructing the mobile device to begin the exertion measurement, generating a measurement bone conduction signal, causing the electro-acoustic transducer to transmit the measurement bone conduction signal through the at least one bone of the body of the user while the user contracts the at least one muscle, receiving, via the electro-acoustic transducer, a modified measurement bone conduction signal, wherein the modified measurement bone conduction signal comprises the measurement bone conduction signal as modified by the body of the user while the user contracts the at least one muscle of the body of the user, and comparing the modified measurement bone conduction signal to the modified baseline bone conduction signal to obtain the muscle exertion data indicative of the level of exertion experienced by the at least one muscle.

7. The mobile device of claim 6, wherein the operations further comprise providing the level of exertion experienced by the at least one muscle to an application; and executing the application to utilize the level of exertion to perform an operation.

8. The mobile device of claim 6, wherein the operations further comprise causing the muscle exertion data to be stored.

9. The mobile device of claim 8, wherein causing the muscle exertion data to be stored comprises causing the muscle exertion data to be stored in the memory.

10. The mobile device of claim 8, further comprising a network component; and wherein causing the muscle exertion data to be stored comprises causing the muscle exertion data to be stored by a service that is accessible by the mobile device via a network to which the mobile device is connected.

11. A computer-readable storage medium having instructions stored thereon that, when executed by a processor of a mobile device, cause the mobile device to perform operations comprising:

instructing a user to relax at least one muscle;

generating a baseline bone conduction signal;

causing an electro-acoustic transducer of the mobile device to transmit the baseline bone conduction signal through at least one bone of a body of the user while the user relaxes the at least one muscle;

receiving, via the electro-acoustic transducer, a modified baseline bone conduction signal, wherein the modified baseline bone conduction signal comprises the baseline bone conduction signal modified by the body of the user while the user relaxes the at least one muscle responsive to receiving instruction from the mobile device;

receiving an input instructing the mobile device to begin an exertion measurement to obtain muscle exertion data indicative of a level of exertion experienced by the at least one muscle;

in response to receiving the input instructing the mobile device to begin the exertion measurement, generating a measurement bone conduction signal;

causing the electro-acoustic transducer to transmit the measurement bone conduction signal through the at least one bone of the body of the user while the user contracts the at least one muscle;

receiving, via the electro-acoustic transducer, a modified measurement bone conduction signal, wherein the modified measurement bone conduction signal comprises the measurement bone conduction signal as modified by the body of the user while the user contracts the at least one muscle of the body of the user; and comparing the modified measurement bone conduction signal to the modified baseline bone conduction signal to obtain the muscle exertion data indicative of the level of exertion experienced by the at least one muscle.

12. The computer-readable storage medium of claim 11, wherein the operations further comprise:

providing the level of exertion experienced by the at least one muscle to an application; and executing the application to utilize the level of exertion to perform an operation.

13. The computer-readable storage medium of claim 11, wherein the operations further comprise causing the muscle exertion data to be stored.

14. The computer-readable storage medium of claim 13, wherein causing the muscle exertion data to be stored comprises causing the muscle exertion data to be store in a memory of the mobile device or causing the muscle exertion data to be stored by a service that is accessible by the mobile device via a network to which the mobile device is connected.

\* \* \* \* \*